(12) United States Patent
Zhou et al.

(10) Patent No.: US 9,486,781 B2
(45) Date of Patent: Nov. 8, 2016

(54) ETHANOL MANUFACTURING PROCESS OVER CATALYST HAVING IMPROVED RADIAL CRUSH STRENGTH

(71) Applicant: Celanese International Corporation, Irving, TX (US)

(72) Inventors: Zhenhua Zhou, Houston, TX (US); Emily Duff, League City, TX (US); Dheeraj Kumar, Pearland, TX (US); Heiko Weiner, Pasadena, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 123 days.

(21) Appl. No.: 14/492,695

(22) Filed: Sep. 22, 2014

(65) Prior Publication Data

US 2015/0024928 A1  Jan. 22, 2015

Related U.S. Application Data

(62) Division of application No. 13/418,755, filed on Mar. 13, 2012, now Pat. No. 8,927,786.

(51) Int. Cl.

| | | |
|---|---|---|
| *B01J 21/04* | (2006.01) | |
| *B01J 23/62* | (2006.01) | |
| *C07C 29/149* | (2006.01) | |
| *B01J 37/10* | (2006.01) | |
| *B01J 23/14* | (2006.01) | |
| *B01J 23/42* | (2006.01) | |
| *B01J 23/44* | (2006.01) | |
| *B01J 23/745* | (2006.01) | |
| *B01J 23/75* | (2006.01) | |
| *B01J 23/89* | (2006.01) | |
| *B01J 35/00* | (2006.01) | |
| *B01J 35/10* | (2006.01) | |
| *B01J 37/02* | (2006.01) | |
| *B01J 21/08* | (2006.01) | |

(52) U.S. Cl.
CPC .............. *B01J 23/626* (2013.01); *B01J 23/14* (2013.01); *B01J 23/42* (2013.01); *B01J 23/44* (2013.01); *B01J 23/745* (2013.01); *B01J 23/75* (2013.01); *B01J 23/8906* (2013.01); *B01J 23/8913* (2013.01); *B01J 23/8993* (2013.01); *B01J 35/002* (2013.01); *B01J 35/1014* (2013.01); *B01J 35/1019* (2013.01); *B01J 37/0207* (2013.01); *B01J 37/10* (2013.01); *C07C 29/149* (2013.01); *B01J 21/04* (2013.01); *B01J 21/08* (2013.01)

(58) Field of Classification Search
CPC ....................................................... B01J 21/04
USPC ........ 502/327, 312, 314, 315, 316, 319, 321
See application file for complete search history.

(56) References Cited

U.S. PATENT DOCUMENTS

| | | |
|---|---|---|
| 2,607,807 A | 8/1952 | Ford |
| 2,744,939 A | 5/1956 | Kennel |
| 2,882,244 A | 4/1959 | Milton |
| 3,102,150 A | 8/1963 | Hunter et al. |
| 3,130,007 A | 4/1964 | Breck |
| 3,383,311 A | 5/1968 | Groszek |
| 3,478,112 A | 11/1969 | Karl et al. |
| 3,864,284 A | 2/1975 | Clippinger et al. |
| 4,048,096 A | 9/1977 | Bissot |
| 4,317,918 A | 3/1982 | Takano et al. |
| 4,395,576 A | 7/1983 | Kwantes et al. |
| 4,398,039 A | 8/1983 | Pesa et al. |
| 4,399,305 A | 8/1983 | Schreck et al. |
| 4,421,939 A | 12/1983 | Kiff et al. |
| 4,443,639 A | 4/1984 | Pesa et al. |
| 4,480,115 A | 10/1984 | McGinnis |
| 4,514,515 A | 4/1985 | Travers et al. |
| 4,517,391 A | 5/1985 | Schuster et al. |
| 4,550,185 A | 10/1985 | Mabry et al. |
| 4,692,218 A | 9/1987 | Houben et al. |
| 4,777,303 A | 10/1988 | Kitson et al. |
| 4,804,791 A | 2/1989 | Kitson et al. |
| 4,826,795 A | 5/1989 | Kitson et al. |
| 4,985,572 A | 1/1991 | Kitson et al. |
| 4,990,655 A | 2/1991 | Kitson et al. |

(Continued)

FOREIGN PATENT DOCUMENTS

| | | |
|---|---|---|
| EP | 0104197 | 4/1984 |
| EP | 0137749 | 4/1985 |
| EP | 0167300 | 1/1986 |
| EP | 0175558 | 3/1986 |
| EP | 0285420 | 10/1988 |
| EP | 0372847 | 6/1990 |
| GB | 2136704 | 9/1984 |
| JP | 6-116182 | 4/1994 |
| JP | 10-306047 | 11/1998 |
| JP | 11-147845 | 6/1999 |
| JP | 2001-046874 | 2/2001 |
| JP | 2001-157841 | 6/2001 |
| WO | WO 2009/077720 | 6/2009 |
| WO | WO 2009/077729 | 6/2009 |
| WO | WO 2011/053365 | 5/2011 |
| WO | WO 2011/056595 | 5/2011 |

OTHER PUBLICATIONS

Alcala, et al., (2005). Experimental and DFT studies of the conversion of ethanol and acetic acid on PtSn-based catalysts, Journal of Physical Chemistry, 109(6), 2074-2085.

(Continued)

*Primary Examiner* — Elvis O Price
(74) *Attorney, Agent, or Firm* — Kilpatrick Townsend & Stockton LLP

(57) ABSTRACT

Acetic acid is hydrogenation in the presence of a catalyst comprising one or more active metals on a silica support, wherein the catalyst has a radial crush strength of at least 4 N/mm. The one or more active metals may include cobalt, copper, gold, iron, nickel, palladium, platinum, iridium, osmium, rhenium, rhodium, ruthenium, tin, zinc, lanthanum, cerium, manganese, chromium, vanadium, molybdenum and mixtures thereof. Radial crush strength may be improved by steam treating the catalyst support prior to the loading of the one or more active metals.

19 Claims, No Drawings

(56) References Cited

U.S. PATENT DOCUMENTS

| | | | |
|---|---|---|---|
| 4,994,608 A | 2/1991 | Torrence et al. |
| 5,001,259 A | 3/1991 | Smith et al. |
| 5,026,908 A | 6/1991 | Smith et al. |
| 5,061,671 A | 10/1991 | Kitson et al. |
| 5,124,004 A | 6/1992 | Grethlein et al. |
| 5,137,861 A | 8/1992 | Shih et al. |
| 5,144,068 A | 9/1992 | Smith et al. |
| 5,149,680 A | 9/1992 | Kitson et al. |
| 5,155,084 A | 10/1992 | Horn et al. |
| 5,243,095 A | 9/1993 | Roberts et al. |
| 5,350,504 A | 9/1994 | Dessau |
| RE35,377 E | 11/1996 | Steinberg et al. |
| 5,599,976 A | 2/1997 | Scates et al. |
| 5,821,111 A | 10/1998 | Grady et al. |
| 5,945,570 A | 8/1999 | Arhancet et al. |
| 6,049,008 A | 4/2000 | Roberts et al. |
| 6,143,930 A | 11/2000 | Singh et al. |
| 6,204,417 B1 | 3/2001 | Fischer et al. |
| 6,232,352 B1 | 5/2001 | Vidalin et al. |
| 6,294,703 B1 | 9/2001 | Hara et al. |
| 6,462,231 B1 | 10/2002 | Yanagawa et al. |
| 6,495,730 B1 | 12/2002 | Konishi et al. |
| 6,509,180 B1 | 1/2003 | Verser et al. |
| 6,524,993 B2 | 2/2003 | Yamaguchi et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,809,217 B1 | 10/2004 | Colley et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,084,312 B1 | 8/2006 | Huber et al. |
| 7,115,772 B2 | 10/2006 | Picard et al. |
| 7,208,624 B2 | 4/2007 | Scates et al. |
| 7,294,604 B2 | 11/2007 | Dath et al. |
| 7,297,236 B1 | 11/2007 | Vander Griend et al. |
| 7,351,559 B2 | 4/2008 | Verser et al. |
| 7,375,049 B2 | 5/2008 | Hayes et al. |
| 7,425,657 B1 | 9/2008 | Elliott et al. |
| 7,507,562 B2 | 3/2009 | Verser et al. |
| 7,538,060 B2 | 5/2009 | Barnicki et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 7,682,812 B2 | 3/2010 | Verser et al. |
| 7,863,489 B2 | 1/2011 | Johnston et al. |
| 7,884,253 B2 | 2/2011 | Stites et al. |
| 7,888,082 B2 | 2/2011 | Verser et al. |
| 8,071,821 B2 | 12/2011 | Johnston et al. |
| 8,211,821 B2 | 7/2012 | Weiner et al. |
| 8,502,001 B2 | 8/2013 | Daniel et al. |
| 8,524,954 B2 | 9/2013 | Ditzel et al. |
| 8,569,203 B2 | 10/2013 | Weiner et al. |
| 8,669,400 B2 | 3/2014 | Johnston et al. |
| 2003/0077771 A1 | 4/2003 | Verser et al. |
| 2003/0104587 A1 | 6/2003 | Verser et al. |
| 2006/0019360 A1 | 1/2006 | Verser et al. |
| 2006/0127999 A1 | 6/2006 | Verser et al. |
| 2007/0238605 A1 | 10/2007 | Strehlau et al. |
| 2007/0270511 A1 | 11/2007 | Melnichuk et al. |
| 2008/0193989 A1 | 8/2008 | Verser et al. |
| 2008/0207953 A1 | 8/2008 | Houssin et al. |
| 2009/0023192 A1 | 1/2009 | Verser et al. |
| 2009/0166172 A1 | 7/2009 | Casey et al. |
| 2009/0221725 A1 | 9/2009 | Chorney et al. |
| 2009/0281354 A1 | 11/2009 | Mariansky et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029995 A1 | 2/2010 | Johnston et al. |
| 2010/0029996 A1 | 2/2010 | Danjo et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0196789 A1 | 8/2010 | Fisher et al. |
| 2010/0197485 A1 | 8/2010 | Johnston et al. |
| 2010/0197985 A1 | 8/2010 | Johnston et al. |
| 2010/0249479 A1 | 9/2010 | Berg-Slot et al. |
| 2010/0273229 A1 | 10/2010 | Verser et al. |
| 2011/0004033 A1 | 1/2011 | Johnston et al. |
| 2011/0046421 A1 | 2/2011 | Daniel et al. |
| 2011/0060174 A1 | 3/2011 | Studt et al. |
| 2012/0238785 A1 | 9/2012 | Zhou et al. |
| 2013/0217925 A1 | 8/2013 | Chornet et al. |

OTHER PUBLICATIONS

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Ordóñez et al., The role of metal and support sites on the hydrogenation of acetic acid on Ru-based catalysts, 21st NAM San Francisco, CA, Jun. 10, 2009.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Proc. Roy Soc. A314, pp. 473-498 (1970).

Rachmady, Acetic Acid Reduction by H2 on Bimetallic Pt—Fe Catalysts, Journal of Catalysis 209, 87-98 (Apr. 1, 2002), Elsevier Science (USA).

Santori et al.(2000). Hydrogenation of carbonylic compounds on Pt/SiO2 catalysts modified with SnBu4, Studies in Surface Science and Catalysis, 130, 2063-2068.

Spivey et al., "Heterogeneous catalytic synthesis of ethanol from biomass-dervied syngas," Chemical Society Review, 2007, vol. 36, pp. 1514-1528.

Subramani et al., "A Review of Recent Literature to Search for an Efficient Catalytic Process for the Conversion of Syngas to Ethanol," Energy & Fuels, 2008, vol. 22, pp. 814-839.

T. Yokoyama, et al., "Carboxylic Acids and Derivatives", Fine Chemicals through Heterogenous Catalysis, pp. 370-379, Jul. 11, 2008.

ZeaChem, Inc., Technology Overview, Lakewood, Colorado www.zeachem.com, 2008.

Zheng, et al., (2007). Preparation and catalytic properties of a bimetallic Sn-Pt complex in the supercages of NaY zeolite by use of surface organometallic chemistry, Applied Organometallic Chemistry, 21(10), 836-840.

International Search Report and Written Opinion for PCT/US2012/069450 mailed Apr. 5, 2013.

International Preliminary Report on Patentability for PCT/US2012/069450 mailed Sep. 25, 2014.

ETHANOL MANUFACTURING PROCESS OVER CATALYST HAVING IMPROVED RADIAL CRUSH STRENGTH

CROSS REFERENCE TO RELATED APPLICATION

This application is a divisional of U.S. application Ser. No. 13/418,755, filed on Mar. 13, 2012, the entirety of which is incorporated herein by reference.

FIELD OF THE INVENTION

The present invention relates to processes for manufacturing ethanol from acetic acid. More specifically, the present invention relates to a process comprising hydrogenating acetic acid in the presence of a catalyst comprising one or more active metals on a silica support, wherein the catalyst has a radial crush strength of at least 4 N/mm. The radial crush strength of the catalyst may be increased by stream treating the catalyst support.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulose materials, such as corn or sugar cane. Conventional methods for producing ethanol from organic feedstocks, as well as from cellulose materials, include the acid-catalyzed hydration of ethylene, methanol homologation, direct alcohol synthesis, and Fischer-Tropsch synthesis. Instability in organic feedstock prices contributes to fluctuations in the cost of conventionally produced ethanol, making the need for alternative sources of ethanol production all the greater when feed stock prices rise. Starchy materials, as well as cellulose materials, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. The reduction of various carboxylic acids over metal oxides has been proposed by EP 0175558 and U.S. Pat. No. 4,398,039. A summary of some of the developmental efforts for hydrogenation catalysts for conversion of various carboxylic acids is provided in Yokoyama, et al., "Carboxylic acids and derivatives" in: *Fine Chemicals Through Heterogeneous Catalysis*, 2001, 370-379.

U.S. Pat. No. 6,495,730 describes a process for hydrogenating carboxylic acid using a catalyst comprising activated carbon to support active metal species comprising ruthenium and tin. U.S. Pat. No. 6,204,417 describes another process for preparing aliphatic alcohols by hydrogenating aliphatic carboxylic acids or anhydrides or esters thereof or lactones in the presence of a catalyst comprising platinum and rhenium. U.S. Pat. No. 5,149,680 describes a process for the catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes a process for the productions of alcohols by the hydrogenation of carboxylic acids in the presence of a catalyst that comprises a first component which is either molybdenum or tungsten and a second component which is a noble metal of Group VIII on a high surface area graphitized carbon support. U.S. Pat. No. 4,804,791 describes another process for the production of alcohols by the hydrogenation of carboxylic acids in the presence of a catalyst comprising a noble metal of Group VIII and rhenium. U.S. Pat. No. 4,517,391 describes preparing ethanol by hydrogenating acetic acid under superatmospheric pressure and at elevated temperatures by a process using a predominantly cobalt-containing catalyst.

U.S. Pat. No. 7,375,049 describes a catalyst for the dehydrogenation and hydrogenation of hydrocarbons which comprises at least one first metal and at least one second metal bound to a support material. The first metal comprises at least one transition metal, suitably a platinum group metal. Tin is preferred and exemplified as the second metal. The support material must comprise an overlayer, e.g. tin oxide, such that acidic sites on the support material are substantially blocked.

Existing processes suffer from a variety of issues impeding commercial viability including: (i) catalysts without requisite selectivity to ethanol; (ii) catalysts which are possibly prohibitively expensive and/or nonselective for the formation of ethanol and that produce undesirable by-products; (iii) required operating temperatures and pressures which are excessive; and/or (iv) insufficient catalyst life.

SUMMARY OF THE INVENTION

In a first embodiment, the present invention is directed to a process for producing ethanol, comprising hydrogenating acetic acid in a reactor in the presence of a catalyst comprising one or more active metals on a silica support, wherein the catalyst has a radial crush strength of at least 4 N/mm, according to ASTM D6175-03. This test method is to determine the ability of an extruded catalyst to retain physical integrity during use. The radial crush strength may be from 4 N/mm to 12 N/mm.

In a second embodiment, the present invention is directed to a process for producing ethanol, comprising hydrogenating acetic acid in a reactor in the presence of a catalyst comprising one or more active metals on a silica support, wherein the silica support is subjected to steam treatment, preferably at a temperature above 50° C. for a period of time prior to impregnating the one or more metals on the silica support. The stream treatment may occur at a temperature from 50° C. to 300° C. for 0.1 to 200 hours. After the steam treatment but prior to impregnation, the silica support, selected from the group consisting of silica, silica/alumina, calcium metasilicate, pyrogenic silica, high purity silica and mixtures thereof, may comprise at least 0.0001% moisture. At least some of this moisture may be removed by subjecting the silica support to drying. The silica support may be present from 25 to 99 wt. % of the total catalyst and may further comprise 0.1 to 50 wt. % of a support modifier. The active metals may include cobalt, copper, gold, iron, nickel, palladium, platinum, iridium, osmium, rhenium, rhodium, ruthenium, tin, zinc, lanthanum, cerium, manganese, chromium, vanadium, molybdenum or combinations thereof. Hydrogenation conditions include a pressure of 10 to 3000 kPa and a hydrogen to acetic acid molar ratio of greater than 2:1. The acetic acid conversion is greater than 30% with a selectivity to ethanol of greater than 60%.

In a third embodiment, the present invention is directed to a process for producing ethanol, comprising hydrogenating acetic acid in a reactor in the presence of a catalyst comprising silica support subjected to steam treatment, wherein the catalyst has a radial crush strength greater than 50% of a radial crush strength of the silica support prior to steam treatment.

In another embodiment, the present invention is directed to a process for producing ethanol, comprising hydrogenating acetic acid in a reactor in the presence of a catalyst comprising one or more active metals on a support selected from the group consisting of alumina, titania, zirconia, zeolite, carbon, activated carbon, and mixtures thereof, and wherein the catalyst has a radial crush strength greater than 50% of a radial crush strength of the support prior to steam treatment.

In a fourth embodiment, the present invention is directed to a hydrogenation catalyst for converting acetic acid to ethanol, the catalyst comprising: one or more active metals on a silica support, wherein the one or more active metals is selected from the group consisting of cobalt, copper, gold, iron, nickel, palladium, platinum, iridium, osmium, rhenium, rhodium, ruthenium, tin, zinc, lanthanum, cerium, manganese, chromium, vanadium, molybdenum and mixtures thereof, wherein the catalyst has a radial crush strength of at least 4 N/mm. The silica support may be subjected to stream treatment at a temperature above 50° C. for a period of time prior to impregnating the one or more metals on the silica support.

In a fifth embodiment, the present invention is directed to a process for making a catalyst for hydrogenating acetic acid having increased radial crush strength, comprising providing a dry support selected from the group consisting of silica, silica/alumina, calcium metasilicate, pyrogenic silica, high purity silica, and mixtures thereof; subjecting the dry support to treatment with steam at a temperature from 50° C. to 300° C. for a period of time from 0.1 to 200 hours; drying the support such that the support comprises at least 0.5% moisture after treatment; and impregnating the support with the one or more active metals. The catalyst may further be calcined at a temperature from 250° C. to 800° C., optionally for a period from 1 to 12 hours.

DETAILED DESCRIPTION OF THE INVENTION

The present invention relates to processes for producing ethanol that comprise hydrogenating acetic acid and hydrogen in a reactor in the presence of a catalyst comprising one or more active metals or oxides thereof on a silica support, wherein the catalyst has a radial crush strength of at least 4 N/mm. In producing ethanol from hydrogenating acetic acid, it is desirable to use a catalyst that can withstand a high mass flow rate, pressure drop, and/or weight load in the hydrogenation reactor, but which also can be manufactured economically. Many plant shutdowns occur due to the mechanical failure of the catalyst, such as increases in pressure drop in axial reactors or bypass formation in radial reactors, rather than low catalytic activity. Decreases in radial crush strength may occur due to cracks in the support.

Embodiments of the present invention overcome this problem by using supports, such as silica supports, which have been pre-treated to maintain a high radial crush strength for the catalyst despite metal impregnation using a metal/water solution. In one embodiment, the present invention is directed to a process for producing ethanol, comprising hydrogenating acetic acid in a reactor in the presence of a catalyst comprising one or more active metals on a silica support, wherein the silica support is subjected to steam treatment at a temperature above 50° C. for a period of time prior to impregnating the one or more metals on the silica support. In another embodiment, the present invention is directed to a process for producing ethanol, comprising hydrogenating acetic acid in a reactor in the presence of a catalyst comprising a silica support subjected to steam treatment, wherein the catalyst has a radial crush strength greater than 50% of a crush strength of the silica support prior to steam treatment.

The catalyst of the present invention preferably has a radial crush strength of at least 4 N/mm, e.g., at least 5 N/mm, or at least 7.5 N/mm. In one embodiment, the catalyst has a radial crush strength from 4 N/mm to 12 N/mm. In another embodiment, the catalyst has a radial crush strength greater than 50% of the radial crush strength of the silica support prior to steam treatment. For example, if the dry silica support prior to steam treatment or impregnation has a radial crush strength of 10 N/mm, then the catalyst of the present invention has a radial crush strength greater than 5 N/mm.

The catalyst composition for use in the present invention comprises a silica support. In preferred embodiments, the support material is present in an amount from 25 wt. % to 99 wt. %, e.g., from 30 wt. % to 98 wt. % or from 35 wt. % to 95 wt. %, based on the total weight of the catalyst composition. The silica support may be selected from the group consisting of silica, silica/alumina, pyrogenic silica, high purity silica, and mixtures thereof. In general silica supports have lower radial crush strength than other types of supports, thus steam treatment is useful in increasing the radial crush strength of silica supported catalysts. However, steam treatment may also be used for other supports, such as alumina, titania, zirconia, zeolite, carbon, activated carbon, and mixtures thereof.

The surface area of the silica support preferably is at least 50 m$^2$/g, e.g., at least 100 m$^2$/g, at least 150 m$^2$/g, at least 200 m$^2$/g or most preferably at least 250 m$^2$/g. In terms of ranges, the silica support preferably has a surface area from 50 to 600 m$^2$/g, e.g., from 100 to 500 m$^2$/g or from 100 to 300 m$^2$/g. For the purposes of the present specification, surface area refers to BET nitrogen surface area, meaning the surface area as determined by ASTM D6556-04, the entirety of which is incorporated herein by reference.

The silica support also preferably has an average pore diameter from 5 to 100 nm, e.g., from 5 to 30 nm, from 5 to 25 nm or from 5 to 10 nm, as determined by mercury intrusion porosimetry, and an average pore volume from 0.5 to 2.0 cm$^3$/g, e.g., from 0.7 to 1.5 cm$^3$/g or from 0.8 to 1.3 cm$^3$/g, as determined by mercury intrusion porosimetry.

The morphology of the silica support, and hence of the catalyst composition for use herein, may vary widely. In some example embodiments, the morphology of the support and/or of the catalyst may be pellets, extrudates, spheres, spray dried microspheres, rings, pentarings, trilobes, quadrilobes, multi-lobal shapes, or flakes although cylindrical pellets are preferred. Preferably, the support has a morphology that allows for a packing density from 0.1 to 1.0 g/cm$^3$, e.g., from 0.2 to 0.9 g/cm$^3$ or from 0.3 to 0.8 g/cm$^3$. In terms of size, the support preferably has an average particle size, e.g., meaning the diameter for spherical particles or equivalent spherical diameter for non-spherical particles, from 0.01 to 1.0 cm, e.g., from 0.1 to 0.5 cm or from 0.2 to 0.4 cm. Since the one or more active metal(s) that are disposed on or within the support are generally very small in size, those active metals should not substantially impact the size of the overall catalyst particles. Thus, the above particle sizes generally apply to both the size of the support as well as the final catalyst particles.

In some embodiments, the support material may also comprise a support modifier. A support modifier may adjust the acidity of the support material. In one embodiment, support modifiers are present in an amount from 0.1 to 50 wt. %, e.g., from 0.2 to 25 wt. %, from 0.5 to 15 wt. %, or from 1 to 8 wt. %, based on the total weight of the catalyst composition.

For example, the acid sites, e.g. Brønsted acid sites, on the support material may be adjusted by the support modifier to favor selectivity to ethanol during the hydrogenation of acetic acid. The acidity of the support material may be adjusted by reducing the number or reducing the availability of Brønsted acid sites on the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. In particular, the use of a modified support that adjusts the acidity of the support to make the support less acidic or more basic favors formation of ethanol over other hydrogenation products.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof. Acidic support modifiers include those selected from the group consisting of $ZrO_2$, $Nb_2O_5$, $Ta_2O_5$, $Al_2O_3$, $B_2O_3$, $P_2O_5$, and $Sb_2O_3$. The acidic modifier may also include those selected from the group consisting of $WO_3$, $MoO_3$, $Fe_2O_3$, $Cr_2O_3$, $V_2O_5$, $MnO_2$, $CuO$, $Co_2O_3$, and $Bi_2O_3$. Preferred acidic support modifiers include those selected from the group consisting of $WO_3$, $MoO_3$, $ZrO_2$, $Nb_2O_5$, $Ta_2O_5$, and $Al_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$) or calcium oxide ($CaO$). When the basic support modifier comprises calcium metasilicate, in some embodiments, at least a portion of the calcium metasilicate may be in crystalline form.

The catalysts of the invention preferably include one or more active metals or oxides thereof. The one or more active metals are selected from the group consisting of cobalt, copper, gold, iron, nickel, palladium, platinum, iridium, osmium, rhenium, rhodium, ruthenium, tin, zinc, lanthanum, cerium, manganese, chromium, vanadium, and molybdenum. The total metal loading of the one or more active metals is from 0.1 to 25 wt. %, e.g., from 0.5 to 20 wt. %. or from 0.6 to 15 wt. %. In one embodiment, the one or more active metals may include a precious metal that is selected from the group consisting of rhodium, rhenium, ruthenium, platinum, palladium, osmium, iridium and gold. The precious metal may be in elemental form or in molecular form, e.g., an oxide of the precious metal. It is preferred that the catalyst comprises such precious metals in an amount less than 5 wt. %, e.g., less than 3 wt. %, less than 1 wt. % or less than 0.5 wt. %. In terms of ranges, the catalyst may comprise the precious metal in an amount from 0.05 to 10 wt. %, e.g. from 0.1 to 5 wt. %, or from 0.1 to 3 wt. %, based on the total weight of the catalyst.

In another embodiment, the catalyst may comprise two active metals or three active metals. The first metal or oxides thereof may be selected from the group consisting of cobalt, rhodium, rhenium, ruthenium, platinum, palladium, osmium, iridium and gold. The second metal or oxides thereof may be selected from the group consisting of copper, iron, tin, cobalt, nickel, zinc, and molybdenum. The third metal or oxides thereof, if present, may be selected from the group consisting of copper, molybdenum, tin, chromium, iron, cobalt, vanadium, palladium, platinum, lanthanum, cerium, manganese, ruthenium, rhenium, gold, and nickel. Preferably, the third metal is different than the first metal and the second metal. In addition, the first metal and the second metal may be different, and the third metal and the second metal may be different.

The metal loadings of the first, second, and optionally third metals are as follows. The first active metal may be present in the catalyst in an amount from 0.05 to 20 wt. %, e.g. from 0.1 to 10 wt. %, or from 0.5 to 5 wt. %. The second active metal may be present in an amount from 0.05 to 20 wt. %, e.g., from 0.1 to 10 wt. %, or from 0.5 to 8 wt. %. If the catalyst further comprises a third active metal, the third active metal may be present in an amount from 0.05 to 20 wt. %, e.g., from 0.05 to 10 wt. %, or from 0.5 to 8 wt. %. The active metals may be alloyed with one another or may comprise a non-alloyed metal solution, a metal mixture or be present as one or more metal oxides. For purposes of the present specification, unless otherwise indicated, weight percent is based on the total weight the catalyst including metal and support.

Bimetallic catalysts for some exemplary catalyst compositions, excluding cesium and tungsten on the support, include platinum/tin, platinum/ruthenium, platinum/rhenium, platinum/cobalt, platinum/nickel, palladium/ruthenium, palladium/rhenium, palladium/cobalt, palladium/copper, palladium/nickel, ruthenium/cobalt, gold/palladium, ruthenium/rhenium, ruthenium/iron, rhodium/iron, rhodium/cobalt, rhodium/nickel, cobalt/tin, and rhodium/tin. More preferred bimetallic catalysts include platinum/tin, platinum/cobalt, platinum/nickel, palladium/cobalt, palladium/copper, palladium/nickel, ruthenium/cobalt, ruthenium/iron, rhodium/iron, rhodium/cobalt, rhodium/nickel, cobalt/tin, and rhodium/tin.

In some embodiments, the catalyst may be a ternary catalyst that comprises three active metals on a support. Exemplary ternary catalysts, may include palladium/tin/rhenium, palladium/cobalt/rhenium, palladium/nickel/rhenium, palladium/cobalt/tin, platinum/tin/palladium, platinum/tin/rhodium, platinum/tin/gold, platinum/tin/iridium, platinum/cobalt/tin, platinum/tin/chromium, platinum/tin/copper, platinum/tin/zinc, platinum/tin/nickel, rhodium/nickel/tin, rhodium/cobalt/tin and rhodium/iron/tin. More preferably, a ternary catalyst comprises three active metals may include palladium/cobalt/tin, platinum/tin/palladium, platinum/cobalt/tin, platinum/tin/chromium, platinum/tin/copper, platinum/tin/nickel, rhodium/nickel/tin, rhodium/cobalt/tin and rhodium/iron/tin.

Preferably, one or more of the active metals is selected from the Group VIII metals. The Group VIII metal may be selected from the group consisting of iron, cobalt, nickel, ruthenium, rhodium, platinum, palladium, osmium, iridium and combinations thereof. Additional active metals may also be used in some embodiments. Therefore, non-limiting examples of active metals on the present catalyst composition with cesium include platinum/tin/cesium, palladium/tin/cesium, platinum/palladium/tin/cesium, nickel/tin/cesium, platinum/nickel/tin/cesium, iron/platinum/tin/cesium, etc. The active metals may be alloyed with one another or may comprise non-alloyed metal solutions or mixtures.

Process for Making Catalyst

In one embodiment of making the catalyst for use herein, one or more support modifiers, if desired, may be added to the support by mixing or through impregnation. Powdered materials of the modified support or a precursor thereto may be pelletized, crushed and sieved. Drying may also be preformed after the support modifier is added.

The modified or unmodified support chosen for the catalyst composition may be shaped into particles having the desired size distribution, e.g., to form particles having an average particle size in the range from 0.2 to 0.4 cm. The support may be extruded, pelletized, tabletized, pressed, crushed or sieved to the desired size distribution. Any of the known methods to shape the support material into desired size distribution can be employed.

In a preferred method of preparing the catalyst, the dry silica support is subjected to a steam treatment prior to impregnation with the one or more active metals. Preferably, the steam treatment may be carried out at a temperature from 50° C. to 300° C., e.g., from 50° C. to 150° C. or from 50° C. to 80° C. Preferably, the catalyst is subjected to steam treatment from 0.1 to 200 hours. The steam treatment may be carried out at a partial pressure from 100 to 5,000 kPa. The weight of the silica support may increase by at least 0.0001% during steam treatment. Preferably, the weight of the silica support may increase by at least 5 during steam treatment, e.g., by at least 20%, by at least 25%, or by at least 33%.

In one embodiment, the extra moisture content of the steam treated silica support may be removed through evaporation. Moisture in the steam treated silica support may be evaporated under reduced pressure to reach the desired level of moisture. Alternatively, the amount of steam treatment may be controlled such that the desired level of moisture is added without the need for evaporation. Preferably, the moisture content in the steam treated silica support is reduced by at least 50% before the active metals are impregnated. In one exemplary embodiment, radial crush strength remains the same as initial support when the catalyst contains up to 33% moisture.

In a preferred method of preparing the catalyst, the active metals are impregnated onto the modified or unmodified steam treated silica support. A precursor of the active metal preferably is used in the metal impregnation step, such as a water soluble compound or water dispersible compound/complex that includes the active metal. Depending on the metal precursor employed, the use of a solvent, such as water, glacial acetic acid or an organic solvent may be preferred. The next active metal also preferably is impregnated into the support material from a next metal precursor, and so forth. If desired, additional metal precursors may also be impregnated into the support material.

Impregnation occurs by adding, optionally drop wise or spray, any or all the metal precursors, preferably in suspension or solution, to the steam treated silica support. The resulting mixture may then be heated, optionally under vacuum, in order to remove the solvent. Additional drying and calcining may then be performed, optionally with ramped heating, to form the final catalyst composition. Upon heating and/or the application of vacuum, the metals of the metal precursors preferably decompose into their elemental (or oxide) form. In some cases, the completion of removal of the liquid carrier, e.g., water, may not take place until the catalyst is placed into use and calcined, e.g., subjected to the high temperatures encountered during operation. During the calcination step, or at least during the initial phase of use of the catalyst, such compounds are converted into a catalytically active form of the metal or a catalytically active oxide thereof.

Impregnation of the active metals (and optional additional metals) into the support may occur simultaneously (co-impregnation) or sequentially. In simultaneous impregnation, the metal precursors (and optionally additional metal precursors) are mixed together and added to the support material together, followed by drying and calcination to form the final catalyst composition. With simultaneous impregnation, it may be desired to employ a dispersion agent, surfactant, or solubilizing agent, e.g., ammonium oxalate, to facilitate the dispersing or solubilizing of the active metal precursors in the event the two precursors are incompatible with the desired solvent, e.g., water.

In sequential impregnation, the first metal precursor is first added to the support material followed by drying and calcining, and the resulting material is then impregnated with the next metal precursor followed by an additional drying and calcining step to form the final catalyst composition. Additional metal precursors may be added either with the first and/or next metal precursor or a separate third impregnation step, followed by drying and calcination. Combinations of sequential and simultaneous impregnation may be employed if desired.

Suitable metal precursors include, for example, metal halides, amine solubilized metal hydroxides, metal nitrates or metal oxalates. For example, suitable compounds for platinum precursors and palladium precursors include chloroplatinic acid, ammonium chloroplatinate, amine solubilized platinum hydroxide, platinum nitrate, platinum ammonium nitrate, platinum tetra ammonium nitrate, platinum chloride, platinum oxalate, palladium nitrate, palladium tetra ammonium nitrate, palladium chloride, palladium oxalate, sodium palladium chloride, and sodium platinum chloride. A suitable tin precursor is stannous oxalate, stannous chloride, and stannic chloride. Generally, both from the point of view of economics and environmental aspects, aqueous solutions of soluble compounds of platinum are preferred. A particularly preferred precursor to platinum is platinum oxalate. Calcining of the solution with the support and active metal may occur, for example, at a temperature from 250° C. to 800° C., e.g., from 300° C. to 700° C. or from 500° C. to 550° C., optionally for a period from 1 to 12 hours, e.g., from 2 to 10 hours, from 4 to 8 hours or 6 hours.

Process for Hydrogenating Acetic Acid

One advantage of the catalyst for use in the present invention is the stability or activity of the catalyst for producing ethanol. Accordingly, it can be appreciated that the catalyst for use in the present invention is fully capable of being used in commercial scale industrial applications for hydrogenation of acetic acid, particularly in the production of ethanol. In particular, it is possible to achieve a degree of stability such that catalyst activity will have a rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

The raw materials, e.g. acetic acid and hydrogen, fed to the reaction zone used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol and ethyl acetate may be integrated with such processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium*, *Lactobacillus*, *Moorella*, *Thermoanaerobacter*, *Propionibacterium*, *Propionispera*, *Anaerobiospirillum*, and *Bacteriodes*, and in particular, species selected from the group consisting of *Clostridium formicoaceticum*, *Clostridium butyricum*, *Moorella thermoacetica*, *Thermoanaerobacter kivui*, *Lactobacillus delbrukii*, *Propionibacterium acidipropionici*, *Propionispera arboris*, *Anaerobiospirillum succinicproducens*, *Bacteriodes amylophilus* and *Bacteriodes ruminicola*. Optionally in this process, all or a portion of the unfermented residue from the biomass, e.g. lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid feedstock fed to the hydrogenation reaction zone may also comprise other carboxylic acids and anhydrides, as well as aldehyde and/or ketones, such as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 150° C., followed by heating of the combined gaseous stream to the reactor inlet temperature.

The reaction zone, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalyst may be used in conjunction with an inert material to regulate the pressure drop of the reactant stream through the catalyst bed and the contact time of the reactant compounds with the catalyst particles.

The hydrogenation in the reactor may be carried out in either liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2500 kPa, or from 100 kPa to 2250 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 500 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalyst bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1. Generally, the reactor may use an excess of hydrogen, while a secondary hydrogenation reactor may use a sufficient amount of hydrogen as necessary to hydrogenate the impurities. In one aspect, a portion of the excess hydrogen from the reactor is directed to a secondary reactor for hydrogenation. In some optional embodiments, a secondary reactor could be operated at a higher pressure than the hydrogenation reactor and a high pressure gas stream comprising hydrogen may be separated from such secondary reactor liquid product in an adiabatic pressure reduction vessel, and the gas stream could be directed to the hydrogenation reactor system.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

For purposes of the present invention, the term "conversion" refers to the amount of acetic acid in the feed that is converted to a compound other than acetic acid. Conversion is expressed as a percentage based on acetic acid in the feed. The conversion may be at least 30%, e.g., at least 40%, or at least 60%. As stated above, the conversion with sequentially prepared catalyst is greater than the conversion with a simultaneously prepared catalyst. Although catalysts that have high conversions are desirable, such as at least 60%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mol. % of the converted acetic acid is converted to ethanol, we refer to the ethanol selectivity as 60%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. In terms of ethanol, for example, a productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Ethanol may be recovered from the product produced by the present process using suitable separation techniques.

The ethanol separated from the product of the process may be an industrial grade ethanol comprising from 75 to 96 wt. % ethanol, e.g., from 80 to 96 wt. % or from 85 to 96 wt. % ethanol, based on the total weight of the ethanol product. In some embodiments, when further water separation is used, the ethanol product preferably contains ethanol in an amount that is greater than 97 wt. %, e.g., greater than 98 wt. % or greater than 99.5 wt. %. The ethanol product in this aspect preferably comprises less than 3 wt. % water, e.g., less than 2 wt. % or less than 0.5 wt. %.

The ethanol produced by the embodiments of the present invention may be used in a variety of applications including fuels, solvents, chemical feedstocks, pharmaceutical products, cleansers, sanitizers, hydrogenation transport or consumption. In fuel applications, the ethanol may be blended with gasoline for motor vehicles such as automobiles, boats and small piston engine aircraft. In non-fuel applications, the ethanol may be used as a solvent for toiletry and cosmetic preparations, detergents, disinfectants, coatings, inks, and pharmaceuticals. The ethanol and ethyl acetate may also be used as a processing solvent in manufacturing processes for medicinal products, food preparations, dyes, photochemicals and latex processing.

The ethanol may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the ethanol may be esterified with acetic acid. In another application, the ethanol may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least 0.6 nm, and preferred zeolites include dehydration catalysts selected from the group consisting of mordenite, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

The following examples describe the catalysts and processes of this invention.

EXAMPLES

Catalyst A: $SiO_2$—$CaSiO_3$ Catalyst on Steam Treated Support with 33% Moisture 100 g of support material comprising $SiO_2$ with 6 wt. % $CaSiO_3$ was steamed at a temperature of above 50° C. for 3.5 hours. The support was then evaporated under reduced pressure in a rotary evaporator to produce 150 g of 33% moisture steam-treated support. 15 g of this steam treated support was used to create the catalyst. A stock solution of Sn dissolved metal in water was prepared by dissolving 0.21 g of $SnC_2O_4$ and 0.376 g of $NH_4OX$ in 5.5 mL of $H_2O$. A stock solution of Pt dissolved metal was prepared by diluting 1.1 g $PtC_2O_4$ in 5.5 mL $H_2O$. Next, equal volumes of the Pt and Sn stock solutions were mixed and stirred at room temperature for 15 minutes. This mixture was impregnated on the solid to create a metal loading of 1.2 wt. % Sn and 1 wt. % Pt, and the resulting catalyst was then dried in a rotary evaporator and then in an oven for 6 hours at 120° C. Finally, the catalyst was calcined at 350° C. for 6 hours. The catalyst comprises 1 wt. % Pt, 1.2 wt. % Sn on a silica support comprising 6 wt. % $CaSiO_3$.

Catalyst B: 20% Moisture Steam Treated Catalyst

The procedure for making the 33% moisture steam-treated catalyst was followed for making the 20% moisture steam-treated catalyst, except the steam treated support was evaporated to a weight of 125 g. 12.5 g of this steam treated support was used to create the catalyst. The catalyst comprises 1 wt. % Pt, 1.2 wt. % Sn on a silica support comprising 6 wt. % $CaSiO_3$.

Catalyst C: Moisture Steam Treated Dry Support

The procedure for making the 33% moisture steam-treated catalyst was followed for making the moisture steam-treated dry support, except the steam treated support was evaporated at a reduced pressure until the support weight became stable, that is, until no measured weight loss was achieved with subsequent evaporation, i.e. the moisture was less than 1 wt. %. 10 g of this steam treated support was used to create the catalyst. The catalyst comprises 1 wt. % Pt, 1.2 wt. % Sn on a silica support comprising 6 wt. % $CaSiO_3$.

Catalyst D: Dry Support Comparative Catalyst 10 g of support material comprising $SiO_2$ with 6 wt. % $CaSiO_3$ was used to create the catalyst. A stock solution of Sn dissolved metal in water was prepared by dissolving 0.21 g of $SnC_2O_4$ and 0.376 g of $NH_4OX$ in 5.5 mL of $H_2O$. A stock solution of Pt dissolved metal was prepared by diluting 1.10 g $PtC_2O_4$ in 5.5 mL $H_2O$. Next, equal volumes of the Pt and Sn stock solutions were mixed and stirred at room temperature for 15 minutes. This mixture was impregnated on the dry solid to create a metal loading of 1.2 wt. % Sn and 1 wt. % Pt, and the resulting catalyst was then dried in a rotary evaporator and then in an oven for 6 hours at 120° C. Finally, the catalyst was calcined at 350° C. for 6 hours. The catalyst comprises 1 wt. % Pt, 1.2 wt. % Sn on a silica support comprising 6 wt. % $CaSiO_3$.

Radial Crush Strength Measurements

The radial crush strength of the catalysts and a silica support were measured according the ASTM D6175-03, "Standard test method for radial crush strength of extruded catalyst and catalyst carrier particles."

Conversion/Selectivity Measurements

Catalysts A, B, C, and D were placed in separate reactor vessels and dried by heating at 120° C. Feedstock acetic acid vapor was charged to the reactor vessels along with hydrogen and helium as a carrier gas with an average combined gas hourly space velocity (GHSV) of 2430 $hr^{-1}$, a temperature of 250° C., a pressure of 2000 kPa, and mole ratio of hydrogen to acetic acid of 8:1. Product samples are taken and analyzed to determine conversion and selectivity. Analysis of the products is carried out by online gas chromatograph (GC). A three channel compact GC equipped with one flame ionization detector (FID) and 2 thermal conducting detectors (TCD) is used to analyze the feedstock reactant and reaction products. The front channel is equipped with an FID and a CP-Sil 5 (20 m)+WaxFFap (5 m) column and is used to quantify: acetaldehyde; ethanol; acetone; methyl acetate; vinyl acetate; ethyl acetate; acetic acid; ethylene glycol diacetate; ethylene glycol; ethylidene diacetate; and paraldehyde. The middle channel is equipped with a TCD and Porabond Q column and is used to quantify: $CO_2$; ethylene; and ethane. The back channel is equipped with a TCD and Porabond Q column and is used to quantify: helium; hydrogen; nitrogen; methane; and carbon monoxide.

Table 1 summarizes results of the radial crush strength, conversion and selectivity measurements.

TABLE 1

| Catalyst | Support Moisture Content | Radial Crush Strength (N/mm) | Conversion of HOAc (%) | Selectivity to EtOH (%) | Selectivity to EtOAc (%) | EtOH Productivity (g/kg/h) |
|---|---|---|---|---|---|---|
| A | 33% | 10.40 | 76 | 79 | 17 | 698 |
| B | 20% | 6.17 | 77 | 79 | 16 | 732 |
| C | <1% | 6.04 | 75 | 79 | 16 | 670 |
| Comp. D | 0% | 3.35 | 71 | 81 | 15 | 619 |
| Support | 0% | 10.76 | — | — | — | — |

It is observed from these examples that catalysts with steam treated supports have an increased radial crush strength and productivity.

While the invention has been described in detail, modifications within the spirit and scope of the invention will be readily apparent to those skilled in the art. All publications and references discussed above are incorporated herein by reference. In addition, it should be understood that aspects of the invention and portions of various embodiments and various features recited may be combined or interchanged either in whole or in part. In the foregoing descriptions of the various embodiments, those embodiments which refer to another embodiment may be appropriately combined with other embodiments as will be appreciated by one skilled in the art. Furthermore, those skilled in the art will appreciate that the foregoing description is by way of example only, and is not intended to limit the invention.

We claim:

1. A hydrogenation catalyst for converting acetic acid to ethanol, the catalyst comprising:
   one or more active metals on a silica support, wherein the one or more active metals is selected from the group consisting of cobalt, copper, gold, iron, nickel, palladium, platinum, iridium, osmium, rhenium, rhodium, ruthenium, tin, zinc, lanthanum, cerium, manganese, chromium, vanadium, molybdenum and mixtures thereof,
   wherein the catalyst has a radial crush strength of at least 4 N/mm.

2. The catalyst of claim 1, wherein the silica support is subjected to steam treatment at a temperature above 50° C. for a period of time prior to impregnating the one or more metals on the silica support.

3. The catalyst of claim 1, wherein the catalyst is made by:
   providing a dry support selected from the group consisting of silica, silica/alumina, calcium metasilicate, pyrogenic silica, high purity silica, and mixtures thereof;
   subjecting the dry support to treatment with steam at a temperature from 50° C. to 300° C. for a period of time from 0.1 to 200 hours;
   drying the support such that the support comprises at least 0.5% moisture after treatment; and
   impregnating the support with the one or more active metals.

4. The catalyst of claim 3, further comprising calcining the catalyst at a temperature from 250° C. to 800° C., optionally for a period from 1 to 12 hours.

5. The catalyst of claim 1, wherein the radial crush strength is from 4 N/mm to 12 N/mm.

6. The catalyst of claim 1, wherein the silica support has an average particle size from 0.01 to 1.0 cm.

7. The catalyst of claim 1, wherein the support material has a surface area from 50 to 600 $m^2/g$.

8. The catalyst of claim 1, wherein the silica support is selected from the group consisting of silica, silica/alumina, calcium metasilicate, pyrogenic silica, high purity silica, or mixtures thereof.

9. The catalyst of claim 1, wherein the one or more active metals is selected from the group consisting of palladium, iron, cobalt, platinum, tin and combinations thereof.

10. The catalyst of claim 1, wherein the support material is present in an amount from 25 to 99 wt. %, based on the total weight of the catalyst composition.

11. The catalyst of claim 1, wherein the support material further comprises a support modifier, wherein the support modifier is present in an amount from 0.1 to 50 wt. %, based on the total weight of the catalyst composition.

12. The catalyst of claim 11, wherein the support modifier is selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

13. The catalyst of claim 11, wherein the support modifier is calcium metasilicate or calcium oxide.

14. The catalyst of claim 11, wherein the support modifier is selected from the group consisting of $WO_3$, $ZrO_2$, $Nb_2O_5$, $Ta_2O_5$, $Al_2O_3$, $B_2O_3$, $P_2O_5$, $Sb_2O_3$, $MoO_3$, $Fe_2O_3$, $Cr_2O_3$, $V_2O_5$, $MnO_2$, $CuO$, $Co_2O_3$, $Bi_2O_3$, and combinations thereof.

15. The catalyst of claim 3, wherein the treatment with steam is at a temperature from 50° C. to 150° C.

16. The catalyst of claim 3, wherein the treatment with steam is at a partial pressure from 100 to 5,000 kPa.

17. The catalyst of claim 3, wherein the weight of the silica support increases by at least 0.0001% during the treatment with steam.

18. The catalyst of claim 3, wherein the weight of the silica support increases by at least 20% during the treatment with steam.

19. The catalyst of claim 3, wherein the support comprises from 0.5 to 33% moisture after the drying.

* * * * *